(12) United States Patent
Deslauriers et al.

(10) Patent No.: US 8,338,498 B2
(45) Date of Patent: Dec. 25, 2012

(54) POLYMERIC BONE DEFECT FILLER

(75) Inventors: Richard J. Deslauriers, Woodbury, CT (US); Eric Kolb, Sandy Hook, CT (US); John Boxberger, Sandy Hook, CT (US)

(73) Assignee: Doctors Research Group, Inc., Southbury, CT (US)

( * ) Notice: Subject to any disclaimer, the term of this patent is extended or adjusted under 35 U.S.C. 154(b) by 132 days.

(21) Appl. No.: 12/708,019

(22) Filed: Feb. 18, 2010

(65) Prior Publication Data

US 2011/0201711 A1  Aug. 18, 2011

(51) Int. Cl.
*C08L 75/04* (2006.01)
(52) U.S. Cl. ..... 521/137; 424/423; 521/170; 623/16.11; 623/23.48; 623/23.51
(58) Field of Classification Search .................. 521/137, 521/170; 424/423; 623/16.11, 23.48, 23.51
See application file for complete search history.

(56) References Cited

U.S. PATENT DOCUMENTS

| 4,645,503 A | 2/1987 | Lin et al. |
| 4,963,151 A | 10/1990 | Ducheyne et al. |
| 6,210,715 B1 | 4/2001 | Starling et al. |
| 6,949,251 B2 | 9/2005 | Dalal et al. |
| 7,094,371 B2 | 8/2006 | Lo |
| 7,357,941 B2 | 4/2008 | Dalal et al. |
| 7,390,498 B2 | 6/2008 | Dalal et al. |
| 7,517,489 B2 | 4/2009 | Akash |
| 2006/0136071 A1 | 6/2006 | Maspero et al. |
| 2008/0069852 A1 | 3/2008 | Shimp et al. |
| 2009/0130173 A1 | 5/2009 | Behnam et al. |
| 2010/0068171 A1* | 3/2010 | Guelcher et al. ........... 424/78.37 |
| 2010/0112032 A1* | 5/2010 | Guelcher et al. .............. 424/423 |

FOREIGN PATENT DOCUMENTS

WO    WO 2009/141732    * 11/2009

OTHER PUBLICATIONS

Karageorgiou et al., "Porosity of 3D biomaterial scaffolds and osteogenesis", Biomaterials, vol. 26, (2005), Elsevier Ltd., pp. 5471-5491.
O.C.M. Pereira-Junior et al., "Comparison Between Polyurethanes Containing Castor Oil (Soft Segment) and Cancellous Bone Autograft in the Treatment of Segmental Bone Defect Induced in Rabbits", Journal of Biomaterials Applications, vol. 21, Jan. 2007, pp. 283-297.
Search Report and Written Opinion from corresponding International Appln. No. PCT/US2011/025196 dated Nov. 23, 2011 (6 pages).

* cited by examiner

*Primary Examiner* — John Cooney
(74) *Attorney, Agent, or Firm* — McCormick, Paulding & Huber LLP

(57) ABSTRACT

A bone defect filler for implantation in a bone defect of a patient includes a particulate polymer distributed within a polymeric binder. The particulate polymer includes a plurality of particles, which may have substantially the same material composition as the polymeric binder. The particles of the particulate polymer may be formed in a variety of shapes and/or sizes to provide the bone defect filler with improved pore interconnectivity, material expansion and contamination characteristics, while maintaining sufficient mechanical strength and handling characteristics for bone repair applications. The bone defect filler also provides the flexibility to be molded or shaped in situ to fill the bone defect.

16 Claims, 12 Drawing Sheets

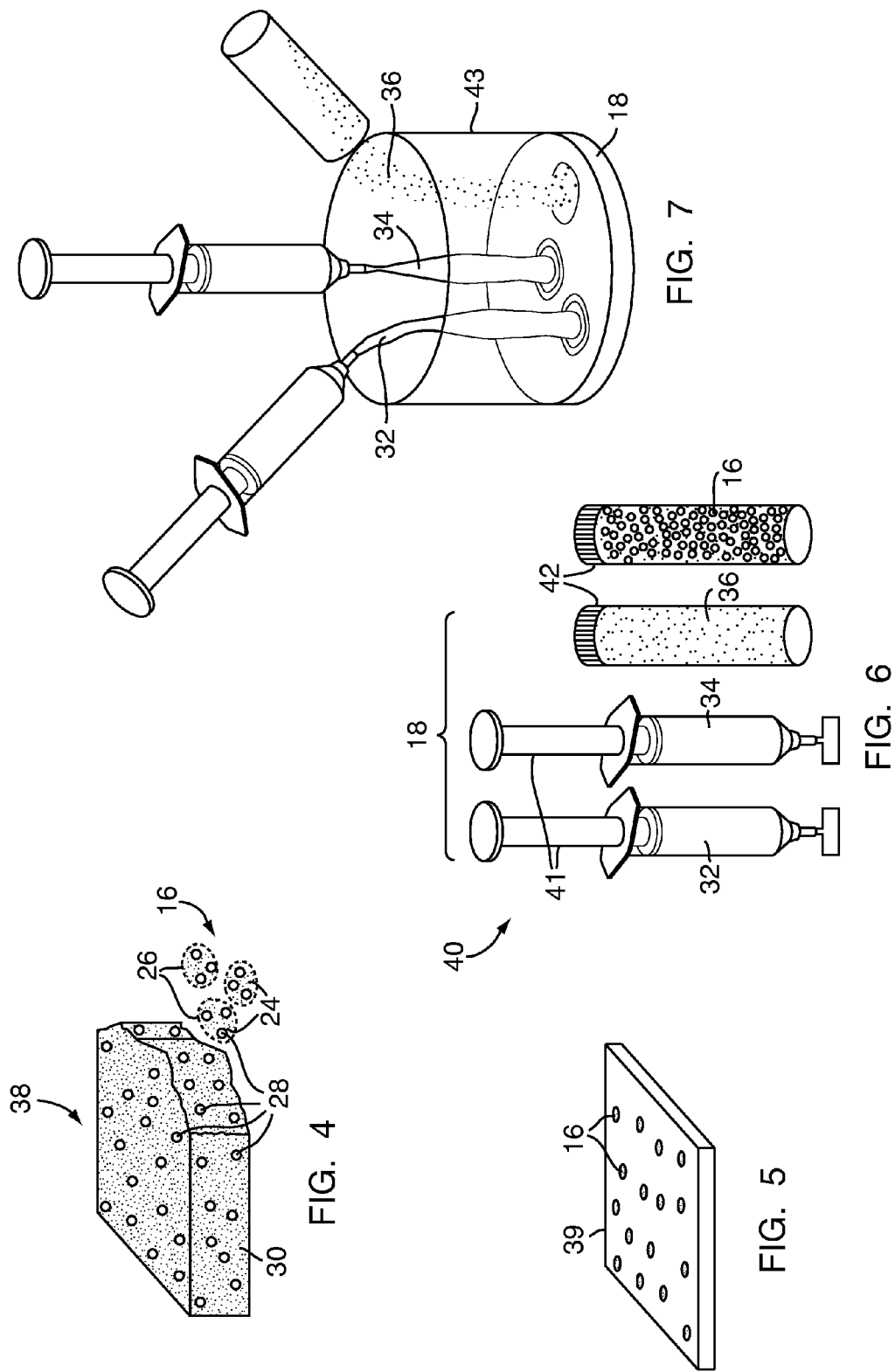

POLYMERIC BONE DEFECT FILLER

FIELD OF THE INVENTION

The present invention relates to compositions for use in bone repair and methods of forming said compositions and, more particularly, to bone repair compositions formed from synthetic bone polymers.

BACKGROUND OF THE INVENTION

There are many situations in which defects in bones or portions of bones must be repaired or replaced, including fractures, joint degeneration, abnormal bone growth, infection and the like. For instance, a bone fracture may result in a portion of missing bone that must be replaced. Similarly, an infection may result in the removal of a portion of bone also requiring replacement.

Conventional bone replacement technologies have developed bone defect fillers for repairing bones by filling bone voids, gaps, cracks and the like. For instance, synthetic bone defect fillers, which are resorbable and porous, may replace bone with a bone-like mineral, e.g. crystalline hydroxyapatite or tricalcium phosphate. The resorbable and porous properties of these synthetic bone defect fillers allow for bone remodeling following implantation. However, conventional synthetic bone defect fillers are problematic because they may have poor tensile, flexural, and shear properties and may adhere poorly to the surrounding bone, which can result in washout of the bone defect filler from the bone defect prior to ingrowth of new bone into the bone defect filler.

Another conventional bone replacement technology includes bone defect fillers with a composition that maintains its chemical and mechanical properties without change or subsequent remodeling (e.g., titanium, stainless steel, PMMA). However, these permanent bone defect fillers are problematic because, inter alia, they are not resorbable and/or cannot be molded and shaped for in situ curing.

Another conventional bone replacement technology includes particulate polymers that can be mixed with blood to fill bone defects. These particulate polymer bone defect fillers are able to substantially conform to the shape of the bone defect, but they have no adhesive properties to adhere the particulate polymer to surrounding bone and, therefore, may wash out of the bone defect. Additionally, particulate polymer bone defect fillers are also problematic because they initially have no structural properties, e.g. tensile and compressive strength, after implantation.

Polyurethane bone defect fillers have also been developed for repairing bone defects. These polyurethane bone defect fillers may advantageously be applied to the bone defect and allowed to cure in situ to provide improved tensile strength and adhesive characteristics over other conventional synthetic bone defect fillers. Additionally, polyurethane bone defect fillers may be formed with a porous structure for promoting new bone ingrowth. However, polyurethane bone defect fillers may be difficult for a doctor to work because the polyurethane may expand as it cures and is typically applied while substantially liquid and, therefore, may fall/run out of the application site. Additionally, care must be taken while curing polyurethane bone defect fillers to avoid contamination, which can increase expansion, decrease adhesive characteristics and/or decrease mechanical strength. The porous structure formed by the polyurethane bone defect filler also typically lacks a high degree of pore interconnectivity, which, if increased, could better promote bone ingrowth after implantation.

Accordingly, there is a need for a polymeric bone defect filler providing increased bone growth promotion and improved handling, implantation and load supporting characteristics.

SUMMARY OF THE INVENTION

According to the present invention, a bone defect filler having a particulate polymer and a polymeric binder may be implanted in a bone defect of a patient. The bone defect filler provides improved pore interconnectivity for bone ingrowth, improved material expansion and contamination characteristics, which are beneficial for handling and implantation, while maintaining sufficient mechanical strength for bone repair applications.

According to some embodiments of the present invention, the particulate polymer and the polymeric binder have substantially the same material composition.

According to some embodiments of the present invention, the polymeric binder may be substantially liquid with the particulate polymer distributed therein.

According to another embodiment of the present invention, a kit for forming the bone defect filler includes a prepolymer and a polyol for mixing to form the polymeric binder. The kit also includes the particulate polymer, which may be mixed with the polymeric binder to form the bone defect filler.

According to some embodiments of the present invention, the kit also includes a non-reactive filler material for mixing with the prepolymer and the polyol to form the polymeric binder.

According to some embodiments of the present invention, the particulate polymer included in the kit is formed from substantially the same prepolymer, polyol and optional non-reactive filler as those included in the kit for formation of the polymeric binder.

These and other objects, features and advantages of the present invention will become apparent in light of the following detailed description of non-limiting embodiments, with reference to the accompanying drawings.

BRIEF DESCRIPTION OF THE DRAWINGS

FIG. 4 is a perspective view of an embodiment for forming a particulate polymer of the bone defect filler of FIG. 1;

FIG. 5 is a perspective view of a mold for forming the particulate polymer of the bone defect filler of FIG. 1 according to another embodiment of the present invention;

FIG. 6 is a perspective view of a kit for forming the bone defect filler of FIG. 1;

FIG. 7 is a perspective view of an embodiment for forming a polymeric binder of the bone defect filler of FIG. 1;

DETAILED DESCRIPTION OF A PREFERRED EMBODIMENT

Figure 1:
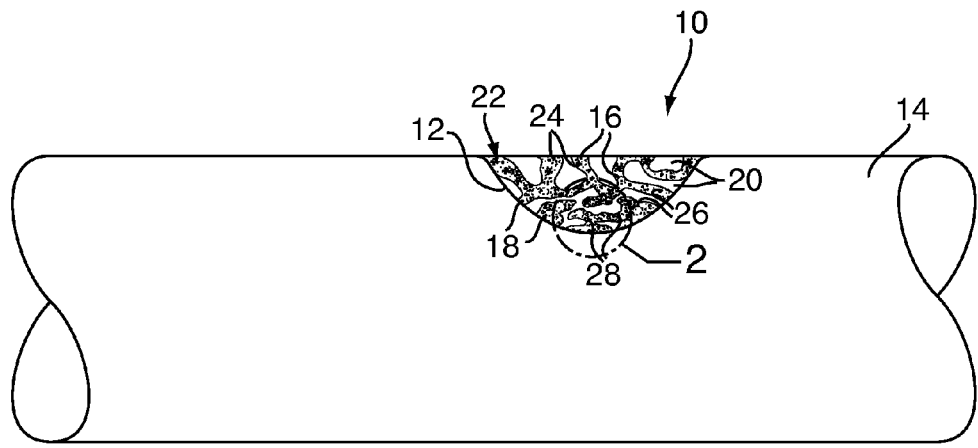
FIG. 1 is a perspective view of an implanted bone defect filler according to an embodiment of the present invention.

Referring to FIG. 1, a bone defect filler 10, for repairing a defect 12 in a bone 14 of a patient, includes a particulate polymer 16 mixed with a polymeric binder 18. The bone defect filler 10 may have a plurality of voids 20, dispersed therein, providing the bone defect filler 10 with a porous structure 22 to promote bone ingrowth and osteoconduction after implantation in the patient.

Figure 2A:
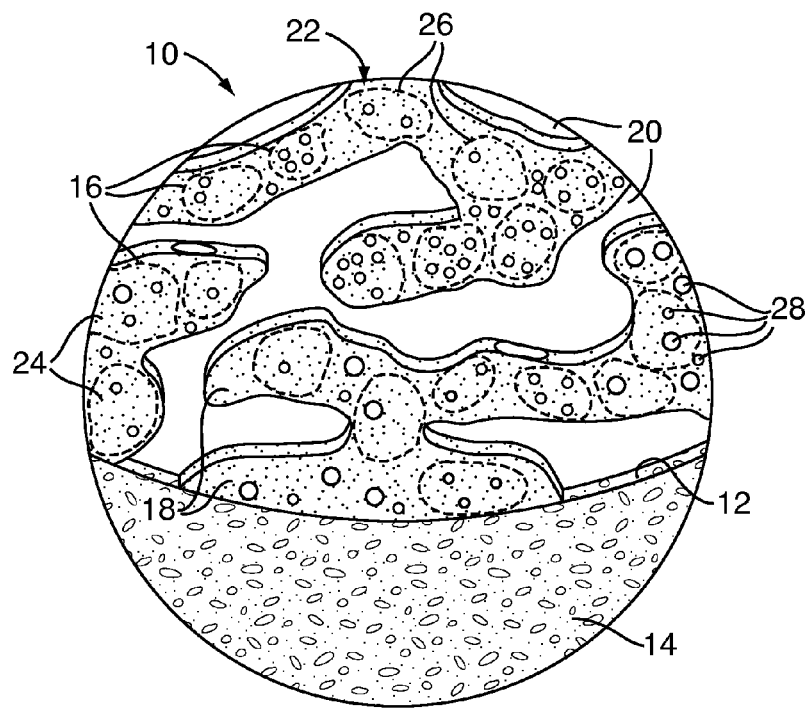
FIG. 2A is an enlarged perspective view of a portion of the implanted bone defect filler of FIG. 1.

Referring to FIG. 2A, the particulate polymer 16 comprises a plurality of particles 24, which may be granular particles 26, having a generally round shape. The voids 20 forming the porous structure 22 are dispersed within the bone defect filler 10 between the particles 24 of the particulate polymer 16. The porous structure 22 of the bone defect filler 10 may include pores 28 formed within the particles 24 of the particulate polymer 16 and within the polymeric binder 18, as will be discussed in greater detail below. The particulate polymer 16 and the polymeric binder 18 are preferably a biocompatible polyurethane material 30, shown in FIG. 3.

Figure 3:
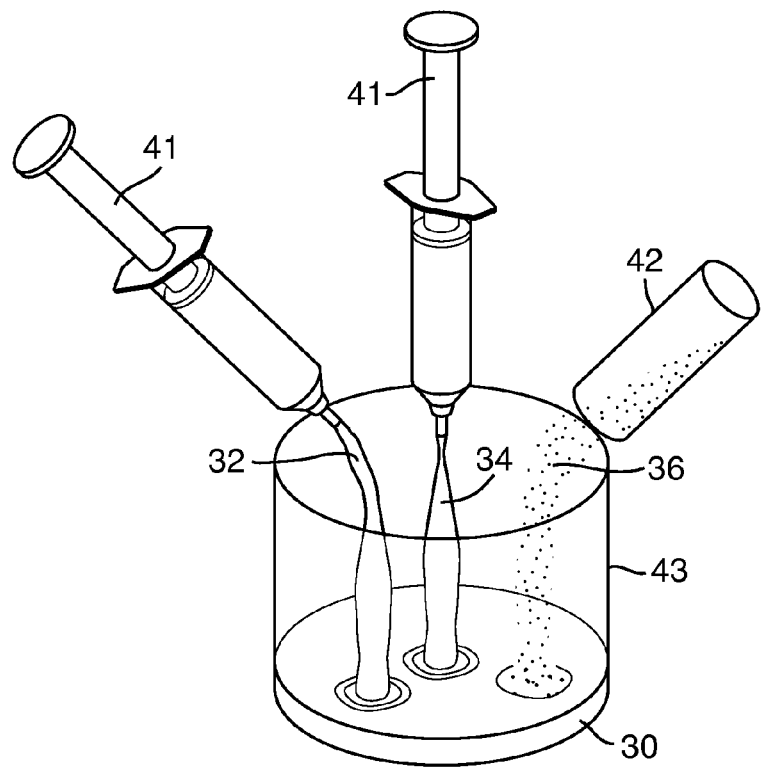
FIG. 3 is a perspective view of an embodiment for forming a biocompatible polyurethane material of the bone defect filler of FIG. 1.

Referring to FIG. 3, the biocompatible polyurethane material 30 may be formed by combining a prepolymer component 32 and a polyol component 34, along with an optional filler material 36, and permitting the combination to react to form the biocompatible polyurethane material 30. An example of one suitable biocompatible polyurethane material 30 for the particulate polymer 16 and the polymeric binder 18 is the KRYPTONITE™ bone matrix product, available from DOCTORS RESEARCH GROUP, INC. of Southbury, Conn., which is described in U.S. patent application Ser. No. 11/089,489, which is hereby incorporated by reference in its entirety.

The prepolymer component 32 for forming the biocompatible polyurethane material 30 includes prepolymer molecules formed by reacting diisocyanate with polyol. The prepolymer component 32 may be a true prepolymer, formed with a two to one ratio of diisocyanate to polyol, or the prepolymer component 32 may be a quasi-prepolymer, formed with a ratio of diisocyanate to polyol in excess of two to one. As will be understood by those skilled in the art, a broad variety of diisocyanates and polyols may be suitable for use in the prepolymer component 32 and the biocompatible polyurethane material 30 of the present invention. Both aromatic and aliphatic diisocyanates may be used to form the prepolymer component 32 of the present invention. The polyol used to form the prepolymer component may be the same as or different than the polyol of the polyol component 34. Additionally, the polyol used to form the prepolymer component 32 may be a blend of different polyols to achieve desired properties. Various polyols suitable for synthesis with the diisocyanate will be discussed in greater detail below.

The polyol component 34 for forming the biocompatible polyurethane material 30 may include naturally occurring polyols and biocompatible, synthetic polyols, and mixtures thereof to achieve desired properties in the biocompatible polyurethane material 30. The polyol component 34 preferably also includes a catalyst for controlling and/or reducing the time required for polymerization of the biocompatible polyurethane material 30. Additionally, the polyol component 34 may include water, which is known to react with diisocyanate to produce carbon dioxide. Thus, the water may be provided to react with the diisocyanate to generate a sufficient amount of carbon dioxide to impart a degree of porosity to the biocompatible polyurethane material 30, as will be discussed in greater detail below. Alternatively, rather than including water in the polyol component 34, moisture from the atmosphere or moisture included in the optional filler material 36 may impart the degree of porosity to the biocompatible polyurethane material 30. Additionally, in instances where moisture is provided from the atmosphere or within the optional filler material 36, it may be desirable to dry the polyols to provide improved control over the amount of carbon dioxide produced and, therefore, the degree of porosity imparted to the biocompatible polyurethane material 30.

The optional filler material 36 for forming the biocompatible polyurethane material 30 may include, but is not limited to, calcium carbonate, bone (e.g., demineralized bone, allograft bone, and/or autogenous bone), calcium phosphate, calcium pyrophosphate, hydroxyapatite, poly methyl methacrylate, glass-ionomer, calcium sulfate, tricalcium phosphate (e.g., beta tricalcium phosphate), or any combination thereof, or the like. In certain embodiments, the filler material 36 may be chosen so as to impart a desired degree of porosity to the biocompatible polyurethane material 30. For example, the filler material 36 may include water for reacting with the diisocyanate of the prepolymer component 32 to generate carbon dioxide and impart the porosity to the biocompatible polyurethane material 30. The filler material 36 may also be present in the biocompatible polyurethane material 30 in an amount sufficient to modify the biocompatible polyurethane material's mechanical properties (e.g., compressive strength, compressive modulus, Young's Modulus of Elasticity, flexural strength, and the like). The filler material 36 may also comprise calcium carbonate and, in certain of these embodiments, the filler material 36 may comprise calcium carbonate in an amount sufficient to provide free calcium to a body of a mammal and enhance osteoconductivity.

Although the biocompatible polyurethane material 30 may be formed with a variety of compositions to achieve desired properties, preferably, the prepolymer component 32 includes aromatic pMDI diiscyanates synthesized with polyols derived from castor oil. The polyol component 34 preferably also includes polyols derived from castor oil and a small percentage of tin based acid as a catalyst. The optional filler material 36 is preferably calcium carbonate powder, at a concentration of thirty percent (30%) by weight, with approximately ninety percent (90%) of the powdered particles being less than ten microns (10 μm) in diameter.

The biocompatible polyurethane material 30 is initially prepared in a liquid state when the prepolymer component 32, polyol component 34 and optional filler material 36 are combined. As the biocompatible polyurethane material 30 cures, it passes through a taffy-like state, in which the biocompatible polyurethane material 30 is easily malleable and may be shaped and sculpted to a desired geometry. The biocompatible polyurethane material 30 then cures into a final solid state.

For simplicity, the particulate polymer 16 and the polymeric binder 18 will be described herein as being formed from biocompatible polyurethane material 30 having substantially the same formulation. Forming the particulate polymer 16 and the polymeric binder 18 from the same biocompatible polyurethane material 30 may be particularly advantageous because the particulate polymer 16 and the polymeric binder 18 will be formed with substantially the same stress and strain properties, which may reduce stress concentrations within the cured bone defect filler 10 and increase product life of the bone defect filler 10. However, it should also be understood by those skilled in the art that the particulate polymer 16 and the polymeric binder 18 may be biocompatible polyurethane materials 30 formed from different prepolymer components 32, polyol components 34, optional filler components 36 and/or combinations thereof.

Referring to FIG. 4, the particulate polymer 16 may be initially formed as a polymeric volume 38 of biocompatible polyurethane material 30 by combining the prepolymer component 32, polyol component 34 and, if desired, the optional filler material 36, as discussed above in connection with FIG. 3, and allowing the combination to polymerize. As discussed above, carbon dioxide byproducts are released during polymerization, at least a portion of which form bubbles within the biocompatible polyurethane material 30 and cure therein, thereby forming the pores 28 within the cured polymeric volume 38. The polymeric volume 38 may then be broken or divided into the particles 24 of the particulate polymer 16, for example by grinding and screening the particles 24 to isolate only particles 24 of a desired size and/or shape. Alternatively, the particles 24 of the particulate polymer 16 may simply be formed with the desired particle size and shape, for example, by providing a mold 39, as shown in FIG. 5, within which to form the granular particles 26. Once the particulate polymer 16 is formed, it may be sterilized, for example, with gamma radiation, and packaged for future mixing to form the bone defect filler 10.

Although the particulate polymer 16 has been described as being formed from a biocompatible polyurethane material 30 by combining the prepolymer component 32, the polyol component 34 and, if desired, the optional filler material 36, as should be understood by those skilled in the art, the particulate polymer 16 may alternatively be formed from polyurethanes having single component formulations. For example, single component polyurethane formulations are known that cure under exposure to moisture or by activating a chemically blocked isocyanate. Accordingly, such single component polyurethane formulations may be used to form the biocompatible polyurethane material 30 for the particulate polymer 16.

Referring back to FIG. 2A, the porosity of the particles 24, i.e. the size and concentration of the pores 28, may be controlled during the polymerization process of the particulate polymer 16. For instance, as discussed above, the carbon dioxide byproducts released during polymerization may be controlled, at least in part, by altering the composition of the components of the biocompatible polyurethane material 30. Additionally, since the pores 28 are formed from off-gassing of carbon dioxide during polymerization, controlling the pressure in which the biocompatible polyurethane material 30 is polymerized, allows for further control of the size and concentration of pores 28. For instance, the biocompatible polyurethane material 30 may be cured in a low pressure environment, such as a vacuum, to increase the size of pores 28 or, alternatively, in a high pressure environment, such as a closed mold, to decrease the size of the pores 28. The size of the particles 24 may also serve to control the porosity of the particles 24, since larger particles 24 will be able to accommodate larger pores 28 and/or a greater quantity of pores 28 than smaller particles 24 would be capable of accommodating. The size and/or concentration of pores 28 may also be controlled by the composition of the biocompatible polyurethane material 30 itself, for example, the type and/or the concentration of the filler component 36 may be used to vary the porosity of the particles 24.

Larger pores 28 provide the porous structure 22 of the bone defect filler 10 with increased porosity and/or increased interconnectivity within the porous structure 22 between the voids 20, the pores 28 and/or combinations thereof for improved bone ingrowth. However, the mechanical properties of the bone defect filler 10 may decrease with increasing porosity and interconnectivity of the porous structure 22. Conversely, smaller pores 28 may reduce the porosity and interconnectivity of the porous structure 22 and provide the bone defect filler 10 with better mechanical properties. Therefore, the size of the pores 28 may be dependent upon, and varied for, the intended application of the bone defect filler 10 depending upon whether the bone defect filler 10 requires superior mechanical properties, increased porosity and/or interconnectivity or an intermediate combination thereof.

Figure 2B:
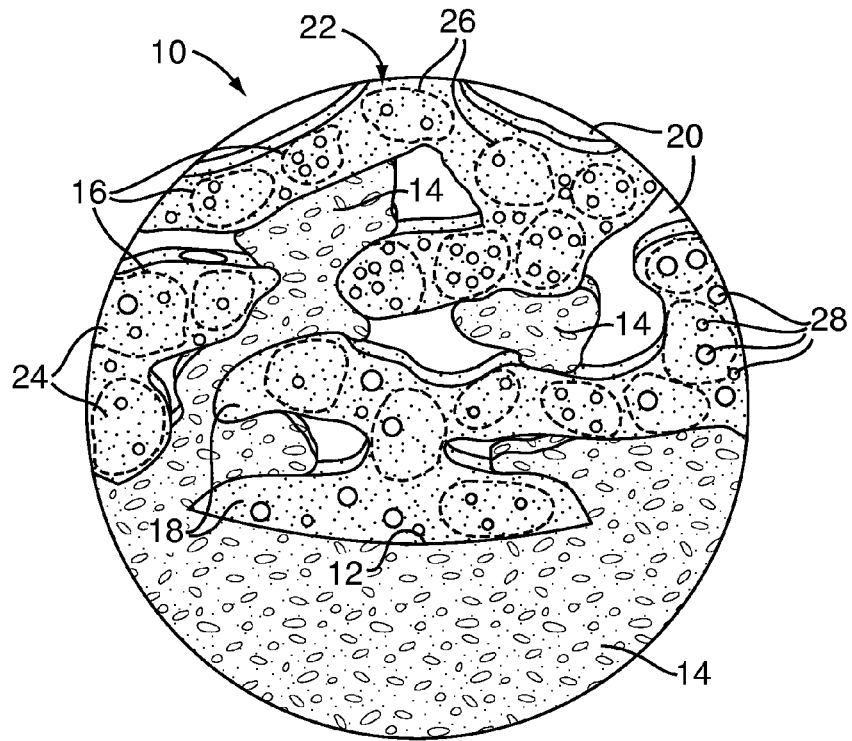
FIG. 2B is the enlarged perspective view of FIG. 2A after bone has begun to grow into the bone defect filler.

Referring to FIG. 2B, preferably, the average size of the pores 28 and voids 20 of the porous structure 22 is at least one hundred microns (100 μm) in diameter to promote ingrowth of bone 14 into the porous structure 22, and, even more preferably, the average size of the pores 28 and voids 20 in the porous structure 22 is greater than three hundred microns (300 μm) in diameter. However, even with an average pore size greater than one hundred microns (100 μm), there may still be pores within the porous structure 22 that are smaller than the one hundred micron (100 μm) average. For example, many of the pores 28 within the particulate polymer 16 are likely to be below the one hundred micron (100 μm) average.

Additionally, it is preferable that the volume of interconnected porosity within the porous structure 22 of the bone defect filler 10 be at least thirty percent (30%) of the total volume of the bone defect filler 10 to allow ingrowth of bone 14 within and through the porous structure 22. Even more preferably, the volume of interconnected porosity within the porous structure 22 of the bone defect filler 10 is at least forty percent (40%) of the total volume of the bone defect filler 10 for the promotion of ingrowth of the bone 14. Methods for determining the percentage of interconnected porosity will be discussed in greater detail below.

Referring to FIG. 6, a kit 40 for forming the bone defect filler 10, shown in FIG. 1, includes the particulate polymer 16, as well as the prepolymer component 32 and polyol component 34 for forming the polymeric binder 18. The kit 40 may also include the optional filler material 36 for forming the polymeric binder 18, if desired. The particulate polymer 16, prepolymer component 32, polyol component 34 and optional filler material 36 are each held in a suitable container such as syringes 41, canisters 42 or the like. The particulate polymer 16 in the kit 40 may include particles 24 of a desired size, shape and/or porosity for an intended application of the bone defect filler 10. Additionally, the kit 40 may include specific quantities of the particulate polymer 16, prepolymer component 32, polyol component 34 and optional filler material 36 to achieve a desired concentration of particulate polymer 16 within the bone defect filler 10. For example, the kit 40 may include a quantity of particulate polymer 16 to achieve a low concentration of particulate polymer 16 in the range of 10% to 30% of the total mass of the bone defect filler 10. Alternatively, the kit 40 may include a quantity of particulate polymer 16 sufficient to achieve a high concentration of particulate polymer 16 in the range of 50% to 70% of total mass of the bone defect filler 10. The quantity of particulate polymer 16 included in the kit 40 may also be sufficient to allow a doctor applying the bone defect filler 10 to mix a variety of desired concentrations prior to application.

Although the concentration of the particulate polymer 16 within the bone defect filler 10 has been described as a percent of the total mass of the bone defect filler 10, it should be understood by those skilled in the art that the concentrations could also be quantified as volume percentages calculated using the equation:

$$Con_{Volume} = \frac{V_{particles}}{V_{Filler}} \times 100$$

where:
$Con_{Volume}$ is the concentration as a percent of volume;
$V_{Particles}$ is a freely-settled bulk volume of the particulate polymer 16 as measured in a graduated cylinder, including the particles 24, internal pores 28 and any interparticle void volume; and
$V_{filler}$ is the volume of the bone defect filler 10, including the particulate polymer 16 and the polymeric binder 18 prior to polymerization.

For instance, the low concentration of particulate polymer 16, when measured as a volume percentage, preferably has a concentration of between 35% and 65% of the total volume of the bone defect filler 10. The high concentration of particulate polymer 16, when measured as a volume percentage, preferably has a concentration between 65% and 90% of the total volume of the bone defect filler 10.

Figure 8:
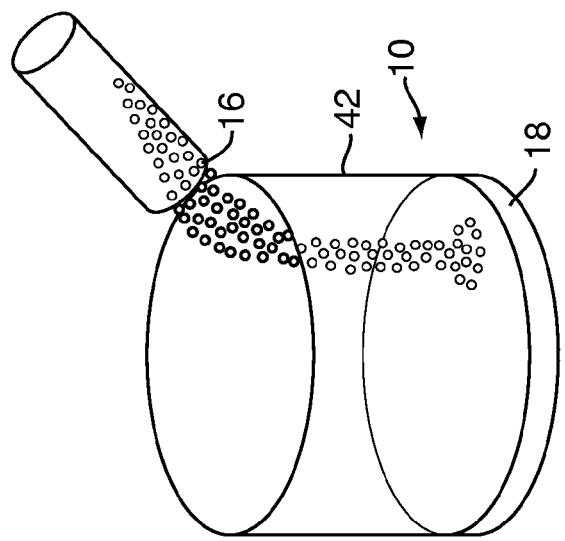
FIG. 8 is a perspective view of an embodiment for forming the bone defect filler of FIG. 1.

Referring to FIG. 7, in operation, the prepolymer component 32, polyol component 34 and optional filler material 36 from the kit 40 are combined and mixed in a suitable vessel 43 to form the polymeric binder 18. Then, referring to FIG. 8, the particulate polymer 16 from the kit 40 is mixed with the polymeric binder 18 to form the bone defect filler 10, shown in FIG. 1. The particulate polymer 16 may be mixed with the polymeric binder 18 while the polymeric binder 18 is in the liquid state of polymerization discussed above, or, alternatively, while the polymeric binder 18 is in the taffy-like state, in which the polymeric binder 18 is easily malleable. Since the particulate polymer 16 is fully cured prior to mixing, it may also simply be combined at the same time as combined with the prepolymer component 32, polyol component 34 and optional filler component 36 for forming the polymeric binder 18.

Once combined, the polymeric binder 18 begins to adhere to the particles 24 of the particulate polymer 16, binding them together. The voids 20 of the porous structure 22 are formed between the particles 24, since there is an insufficient amount of polymeric binder 18 to fill all of the gaps between the particles 24. Thus, the amount of polymeric binder 18 or, alternatively, the concentration and/or particle size of the particulate polymer 16, may be varied to control the size and/or concentration of voids 20 within the bone defect filler 10 and the porosity and interconnectivity of the porous structure 22. For instance, increasing the amount of polymeric binder 18 or decreasing the concentration and/or size of the particulate polymer 16 will decrease the size and/or concentration of voids 20 within the bone defect filler 10. Alternatively, decreasing the amount of polymeric binder 18 or increasing the concentration and/or particle size of the particulate polymer 16 will increase the size and/or concentration of voids 20 within the bone defect filler 10.

Referring back to FIG. 1, the bone defect filler 10 is preferably applied to the defect 12 while the polymeric binder 18 is still in a viscous state, i.e. before the polymeric binder 18 has fully cured. Since the polymeric binder 18 is in a viscous state when applied to the defect 12, the bone defect filler 10 may be molded to a desired shape and/or to conform to the shape of the defect 12. The polymeric binder 18 then cures within the defect 12 to a final solid state, adhering the bone defect filler 10 to the bone 14. As the polymeric binder 18 cures, it off-gasses carbon dioxide in a manner similar to that described above in connection with the curing of the particulate polymer 16. The carbon dioxide from the polymeric binder 18 forms bubbles within the bone defect filler 10, thereby forming pores 28 within the polymeric binder 18.

Referring to FIG. 2A, the combination of the particulate polymer 16 with the polymeric binder 18 allows for the bone defect filler 10 to be formed with a high degree of interconnectivity between the voids 20, pores 28 and/or combinations thereof because the voids 20 form around and between the particles 24 of the particulate polymer 16. The interconnectivity provides the porous structure 22 of the bone defect filler 10 with a substantially open porous structure to better promote bone ingrowth and osteoconduction.

As interconnectivity within the porous structure 22 increases, the mechanical properties of the bone defect filler 10 may decrease. Therefore, the degree of interconnectivity of the porous structure 22 must be balanced with the desired mechanical properties for a given application of the bone defect filler 10. This balance may be achieved by varying the size, shape, concentration and/or porosity of the particulate polymer 16 within the bone defect filler 10.

Additionally, although FIGS. 2A and 2B show a single planar cut through the bone defect filler 10, it should be understood by those skilled in the art that the interconnectivity within the porous structure 22 may occur in different planes than that shown. Thus, some pores 28 and/or voids 20 of the porous structure 22 that may appear to be closed pore in FIGS. 2A and 2B may, in fact, be interconnected with other pores and voids within the three dimensional bone defect filler 10.

Figure 9:
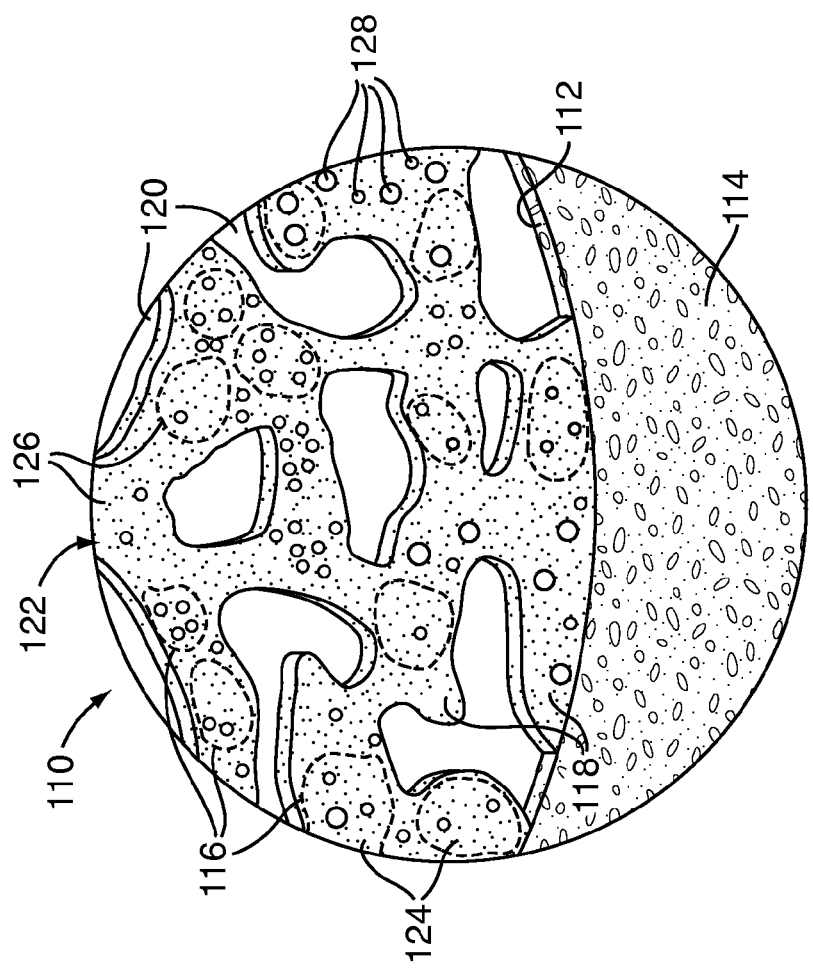
FIG. 9 is a perspective view of implanted bone defect filler according to another embodiment of the present invention.

For instance, referring to FIG. 9, wherein like numerals represent like elements, the concentration of particulate polymer 116 in the bone defect filler 110 may be decreased, thereby decreasing the interconnectivity of voids 120 and pores 128 and increasing the mechanical properties of the bone defect filler 110. Additionally, the decrease in concentration may make the bone defect filler 110 less viscous, thereby easing implantation by enabling the bone defect filler 110 to be injected through a syringe into a bone defect 12. However, this lowered viscosity may also increase the tendency for the bone defect filler 110 to flow out of the bone defect 112 after implantation. Additionally, the decrease in concentration of the particulate polymer 116 may also make the bone defect filler 110 more susceptible to contamination and expansion, as will be discussed in greater detail below.

Figure 10:
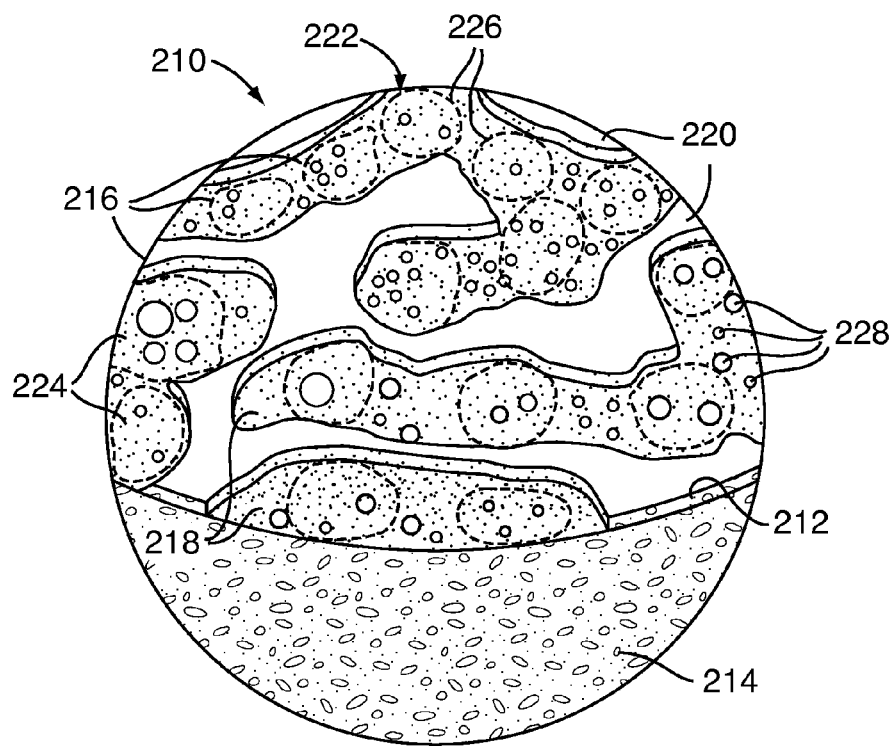
FIG. 10 is a perspective view of implanted bone defect filler according to a further embodiment of the present invention.
Figure 11:
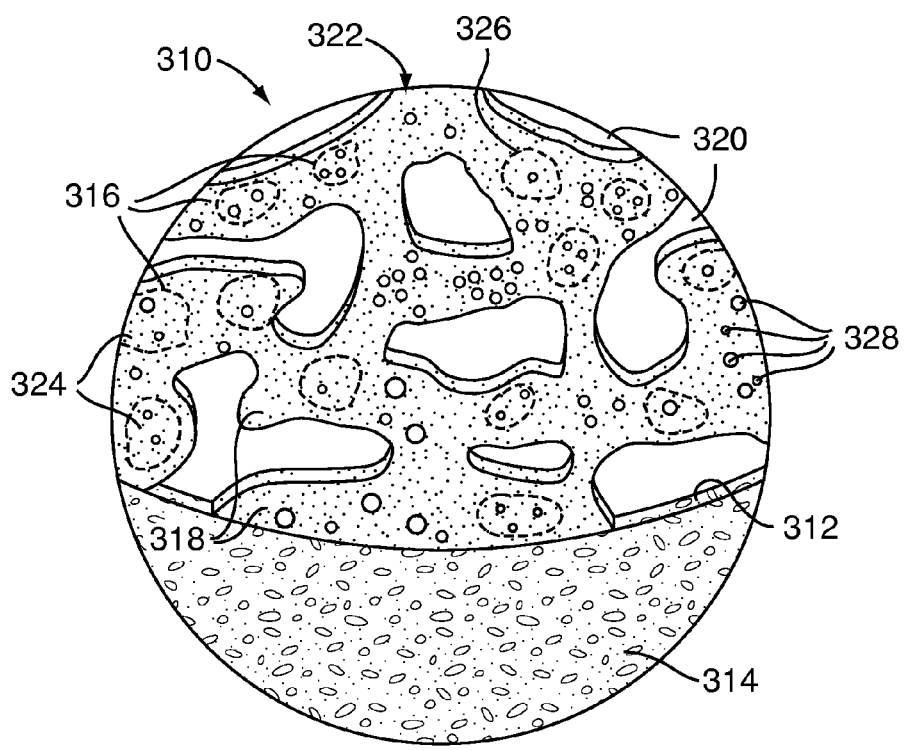
FIG. 11 is a perspective view of implanted bone defect filler according to another embodiment of the present invention.

As discussed above, not only the concentration, but also the size of particles 24 may be varied to affect the properties and characteristics of the bone defect filler 10. For instance, referring to FIG. 10, the size of the particles 224 may be increased to reduce expansion of the bone defect filler 210 and to increase interconnectivity of voids 220 and pores 228. As discussed above, this increase in particle size must be balanced with the corresponding reduction in the mechanical properties of the bone defect filler 210. Larger particles 224 also allow for the formation of larger pores 228 within the particles 224, thereby providing a larger range in which the pore size may be varied to optimize the strength/porosity trade off of the bone defect filler 210. Alternatively, referring to FIG. 11, the particles 324 may be reduced in size to form bone defect filler 310 having lower porous interconnectivity and improved mechanical properties. This reduction in the size of particles 324 also reduces the range of size for formation of the pores 328.

Figure 12:
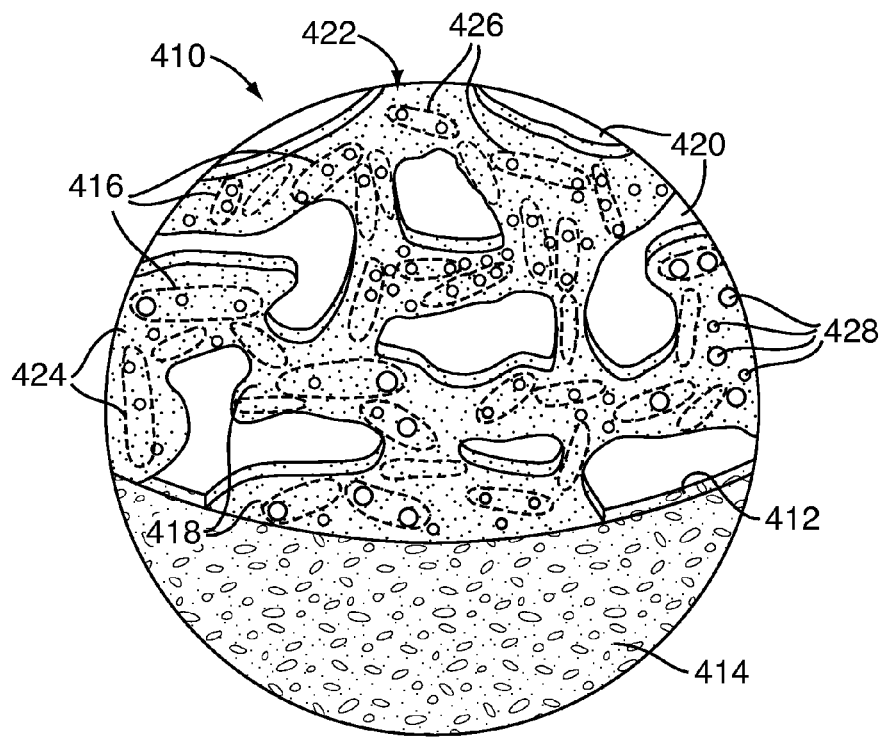
FIG. 12 is a perspective view of implanted bone defect filler according to a further embodiment of the present invention.

The shape of the particles 24 of the particulate polymer 16 may also be selected to provide bone defect filler 10 with desired mechanical properties and characteristics. For instance, Referring to FIG. 12, bone defect filler 410 may have particles 424 that are flake particles 444, with thin elongated bodies, rather than the granular particles 26 of FIG. 1. The flake particles 444 may provide the bone defect filler 410 improved mechanical properties along with reduced porous interconnectivity within the bone defect filler 410.

Figure 13:
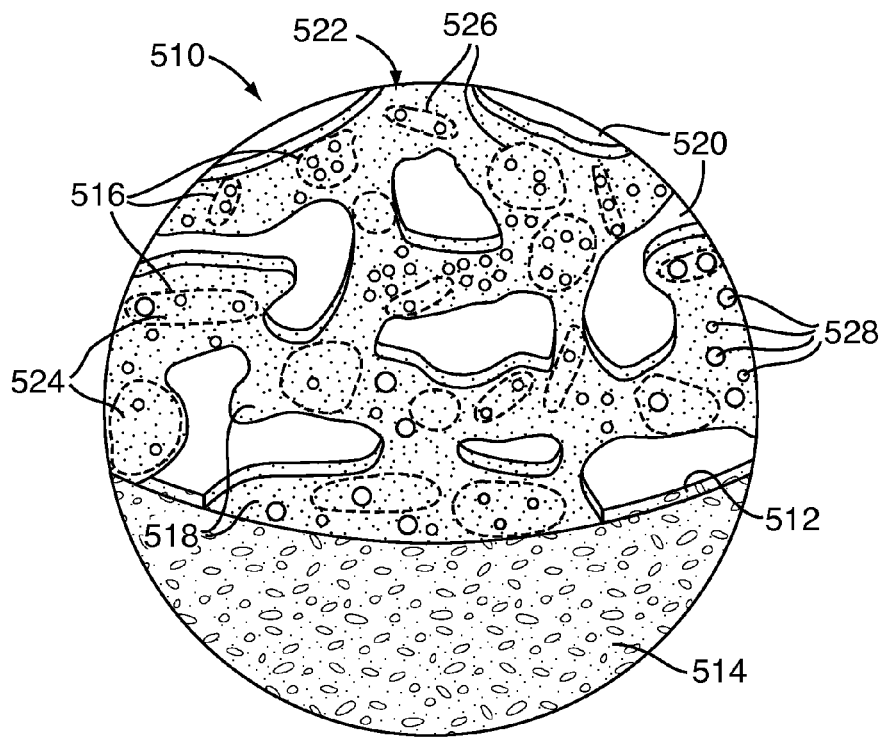
FIG. 13 is a perspective view of implanted bone defect filler according to an additional embodiment of the present invention.

Additionally, while the present invention has been discussed in terms of granular particles 26 and flake particles 444, it should be understood to those skilled in the art that particles 24, 124, 224, 324, 424 may be formed in a variety of other shapes to achieve desired mechanical properties and/or characteristics for the bone defect filler 10, 110, 210, 310, 410. Additionally, the bone defect filler 10, 110, 210, 310, 410 may include particles 24, 124, 224, 324, 424 of a combination of sizes and shapes to achieve desired properties. For example, referring to FIG. 13, bone defect filler 510 may include particulate polymer 516 having granular particles 526 of varied size, i.e. large and small, as well as substantially uniformly sized flake particles 544. While the particulate polymer 516 is shown as having granular particles 526 of varied size and flake particles 544 of uniform size, it should be understood to those skilled in the art that the both the granular particles 526 and the flake particles 544 may be of varied and/or uniform size.

Referring back to FIG. 1, variation of the size, shape and concentration of the particulate polymer 16 may also be used to achieve other desired characteristics from the bone defect filler 10, for example, increased concentration and/or particle size of the particulate polymer 16 may reduce expansion of the bone defect filler 10 within the defect 12. Since the particulate polymer 16 is substantially cured prior to application of the bone defect filler 10, at least a portion of the reduced expansion results from a decrease in the amount of biocompatible material 24 polymerizing, i.e. only the polymeric binder 18 must be polymerized. Additionally, the particulate polymer 16 further reduces expansion by providing space within the bone defect filler 10 between particles 24 within which the polymeric binder 18 may expand internally. This reduction in expansion provides the doctor applying the bone defect filler 10 with greater control of material positioning during the application process.

As the concentration of the particulate polymer 16 in the bone defect filler 10 is increased, the peak exothermic temperature produced during polymerization of the bone defect filler 10 is also reduced. This reduction in peak exothermic temperature may result in a corresponding reduction in cellular damage to the patient and quicker biological recovery.

Increasing the concentration of the particulate polymer 16 within the bone defect filler 10 may also reduce the susceptibility of the bone defect filler 10 to contamination from contaminants that may be present in the environment or in blood during in situ polymerization such as water, oil and the like. For instance, moisture and oil lipids in blood present at an operative site during a bone repair surgery may cause water and oil contamination, respectively. Increasing the concentration of the particulate polymer 16 within the bone defect filler 10 will reduce the susceptibility of the bone defect filler 10 to water contamination since the particulate polymer 16 is hydrophobic when cured. Thus, the particulate polymer 16 will be unaffected by the water contamination, thereby effectively reducing the portion of the bone defect filler 10 that is susceptible to water contamination. Similarly, since the particulate polymer 16 is fully cured, increasing the concentration of the particulate polymer 16 in the bone defect filler 10 will reduce the portion of the bone defect filler 10 that is susceptible to oil contamination by reducing the amount of biocompatible polyurethane material 30 that polymerizes in situ., Since oil is a polyol, contaminant oil may react with a portion of the diisocyanate in the prepolymer component 32 during in situ polymerization rather than the polyol component 34. Since the polyol component 34 is typically selected to impart desired properties to the biocompatible polyurethane material 30, if a portion of the diisocyanate reacts with contaminant oil rather than the polyol component 34, the polymerization process is less controlled and the bone defect filler 10 may be formed with unknown, unwanted and/or inferior properties.

Thus, the particles 24 may be formed to desired sizes, shapes and/or porosities and the concentration of the particulate polymer 16 varied to provide desired properties and/or characteristics to the bone defect filler 10.

The concentration of the particulate polymer 16 within the bone defect filler 10 may also affect the method in which the bone defect filler 10 may be applied to the defect 12. For instance, bone defect filler 10 with a low concentration and particle size of particulate polymer 16 may be injectible through a syringe, since the lower concentration of particulate polymer 16 will result in a less viscous bone defect filler 10 and since the small particles 24 may be able to flow through a Luer-Lok connection and a cannula of the syringe. More viscous bone defect fillers 10 with larger particle sizes and/or higher concentrations of particulate polymer 16 may be implantable by hand or through the use of another bone filler device, such as a spatula or the like.

The following non-limiting Exemplary Embodiments 1-7 of bone defect filler 10 according to the present invention, along with reference to FIGS. 14-25, will aid in demonstrating the features and advantages of various embodiments of the bone defect filler 10 over conventional polyurethane bone defect fillers. In each of the Exemplary Embodiments 1-7, the particulate polymer 16 and the polymeric binder 18 are formed from the preferred composition of the biocompatible polyurethane material 30 discussed above, having the same prepolymer component 32 (30% pMDI diisocyanate and 10% castor oil derived polyol), polyol component 34 (30% castor oil derived polyol and tin based acid catalyst) and filler material 36 (30% calcium carbonate by mass).

Additionally, the particulate polymer 16 for each exemplary embodiment has a standard porosity consistent with being formed within an open mold at ambient pressure. A control polyurethane bone defect filler ("control"), that does not include particulate polymer 16, is also illustrated in FIGS. 14-25 for comparison. The control is also formed from the same material composition as the particulate polymer 16 and the polymeric binder 18 of the bone defect filler 10.

Various properties of the Exemplary Embodiments 1-7 and the control, for both dry formation, i.e. without water contamination, and wet formation, i.e. with water contamination, are shown in FIGS. 14-25.

Exemplary Embodiment 1

Exemplary Embodiment 1 is bone defect filler 10 having a low concentration of powdered granules as the particulate polymer 16. The particles 24 of the particulate polymer 16 of Exemplary Embodiment 1 are less than eight tenths of a millimeter (0.8 mm) in size. Exemplary Embodiment 1 has a twenty percent (20%) concentration of particulate polymer 16 as a percent of total mass and a fifty five percent (55%) concentration of particulate polymer 16 as a percent of total volume. Exemplary Embodiment 1 is readily mixable, and, after initial mixing, handles similarly to the control. Additionally, Exemplary Embodiment 1 is injectable through a large gauge cannula or may be packed into the bone defect 12. When fully cured, Exemplary Embodiment 1 resembles the control in appearance.

Exemplary Embodiment 2

Exemplary Embodiment 2 is bone defect filler 10 having a low concentration of small granules as the particulate polymer 16. The particles 24 of the particulate polymer 16 of Exemplary Embodiment 2 are between eighth tenths of a millimeter and one and six tenths of a millimeter (0.8-1.6 mm) in size. Exemplary Embodiment 2 has a twenty percent (20%) concentration of particulate polymer 16 as a percent of total mass and a sixty three percent (63%) concentration of particulate polymer 16 as a percent of total volume. Exemplary Embodiment 2 mixes well and handles similar to the control after mixing. Additionally, Exemplary Embodiment 2 is injectable through a cannula large enough to allow the granules to pass or may be packed into the bone defect 12. When fully cured, Exemplary Embodiment 2 resembles the control in appearance.

Exemplary Embodiment 3

Exemplary Embodiment 3 is bone defect filler 10 having a low concentration of large granules as the particulate polymer 16. The particles 24 of the particulate polymer 16 of Exemplary Embodiment 3 are between one and six tenths of a millimeter and three and two tenths of a millimeter (1.6-3.2 mm) in size. Exemplary Embodiment 3 has a twenty percent (20%) concentration of particulate polymer 16 as a percent of total mass and a sixty five percent (65%) concentration of particulate polymer 16 as a percent of total volume. Exemplary Embodiment 3 handles similar to the control and can easily flow and be poured or applied via spatula or similar tool to a bone defect 12. However, Exemplary Embodiment 3 is not injectable through a cannula as the particles 24 are too large. When fully cured, Exemplary Embodiment 3 resembles the control in appearance.

Exemplary Embodiment 4

Exemplary Embodiment 4 is bone defect filler 410 having a low concentration of flake particles 444 as the particulate polymer 416. The size of the particles 424 of the particulate polymer 416 of Exemplary Embodiment 4 is less than ten millimeters (10 mm) long by less than three millimeters (3 mm) wide by less than five tenths of a millimeter (0.5 mm) tall. Exemplary Embodiment 4 has a twenty percent (20%) concentration of particulate polymer 416 as a percent of total mass and a sixty five percent (65%) concentration of particulate polymer 16 as a percent of total volume. Exemplary Embodiment 4 is not as readily mixable as the other low concentration Exemplary Embodiments, i.e. Exemplary Embodiments 1-3. After mixing, Exemplary Embodiment 4 is not a flowing liquid and is not injectable. Exemplary Embodiment 4 may be handled with gloves, although some adhesiveness is preserved. When fully cured, Exemplary Embodiment 4 has a random orientation of flake particles 444.

Exemplary Embodiment 5

Exemplary Embodiment 5 is bone defect filler 10 having a high concentration of powder granules as the particulate polymer 16. The particles 24 of the particulate polymer 16 of Exemplary Embodiment 5 are less than eight tenths of a millimeter (0.8 mm) in size. Exemplary Embodiment 5 has a sixty percent (60%) concentration of particulate polymer 16 as a percent of total mass and an eighty one percent (81%) concentration of particulate polymer 16 as a percent of total volume. Exemplary Embodiment 5 requires additional mixing, relative to the control, to fully mix the particulate polymer 16 and the polymeric binder 18. After mixing, Exemplary Embodiment 5 may be handled with gloves and may be packed into or shaped to fit tightly into bone defect 12. When fully cured, Exemplary Embodiment 5 has porosity that is visibly different from the control and Exemplary Embodiments 1-3.

Exemplary Embodiment 6

Exemplary Embodiment 6 is bone defect filler 10 having a high concentration of small granules as the particulate polymer 16. The particles 24 of the particulate polymer 16 of Exemplary Embodiment 6 are between eighth tenths of a millimeter and one and six tenths of a millimeter (0.8-1.6 mm) in size. Exemplary Embodiment 6 has a sixty percent (60%) concentration of particulate polymer 16 as a percent of total mass and an eighty four percent (84%) concentration of particulate polymer 16 as a percent of total volume. Exemplary Embodiment 6 requires additional mixing, relative to the control, to fully mix the particulate polymer 16 and the polymeric binder 18. After mixing, Exemplary Embodiment 6 may be handled with gloves and may be packed into or shaped to fit tightly into bone defect 12. When fully cured, Exemplary Embodiment 6 has porosity that is visibly different from the control and Exemplary Embodiments 1-3.

Exemplary Embodiment 7

Exemplary Embodiment 7 is bone defect filler 10 having a high concentration of large granules as the particulate polymer 16. The particles 24 of the particulate polymer 16 of Exemplary Embodiment 7 are between one and six tenths of a millimeter and three and two tenths of a millimeter (1.6-3.2 mm) in size. Exemplary Embodiment 7 has a sixty percent (60%) concentration of particulate polymer 16 as a percent of total mass and an eighty five percent (85%) concentration of particulate polymer 16 as a percent of total volume. Exemplary Embodiment 7 requires additional mixing, relative to the control, to fully mix the particulate polymer 16 and the polymeric binder 18. After mixing, Exemplary Embodiment 7 may be handled with gloves and may be packed into or shaped to fit tightly into bone defect 12. When fully cured, Exemplary Embodiment 7 has porosity that is visibly different from the control and Exemplary Embodiments 1-3.

The Exemplary Embodiments 1-7 and the control were formed and tested without contamination, according to the compositions discussed above. Additionally, Exemplary Embodiments 1-7 and the control were also formed and tested with water contamination. The compositions of Exemplary Embodiments 1-7 and the control for the tests with water contamination were consistent with those for the tests without water contamination; however, after mixing the particulate polymer 16 into the polymeric binder 18 for approximately one minute, one and six tenths milliliters (1.6 mL) of water was added to the mixture and mixed for approximately forty-five (45) seconds. The tests were then conducting according to the same procedure as used for the tests without water contamination.

Figure 14:
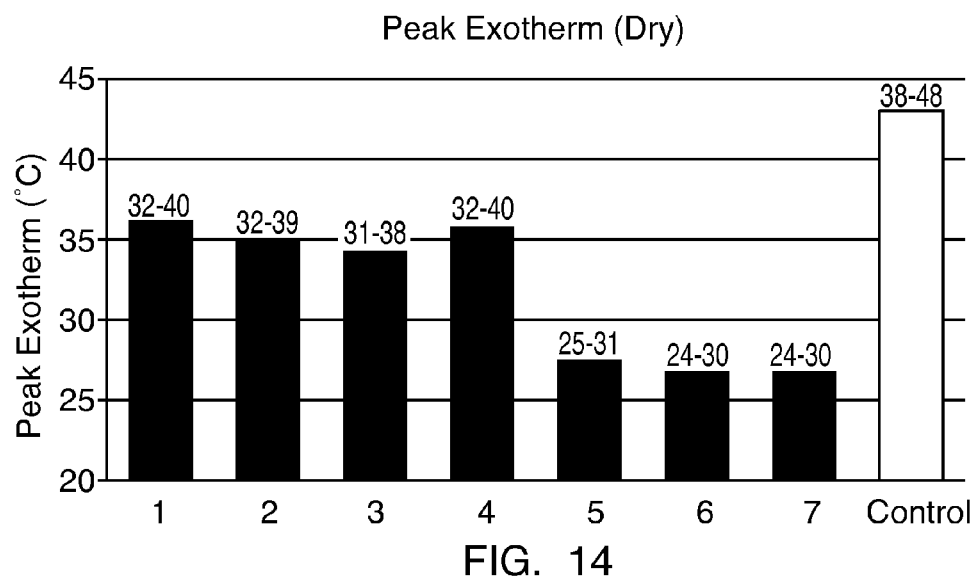
FIG. 14 is a bar graph of peak exothermic temperature produced during polymerization of bone defect filler according to Exemplary Embodiments of the present invention.

Referring to FIG. 14, the peak exothermic temperatures during polymerization at room temperature, without water contamination, of Exemplary Embodiments 1-7 were measured. For Exemplary Embodiments 1-3 and the control, approximately sixteen milliliters (16 mL) of bone defect filler was poured into a fifty-milliliter (50 mL) polypropylene graduated cylinder with a thermocouple mounted on the container surface at the five-milliliter (5 mL) level for measuring the exothermic temperature. For Exemplary Embodiment 4, which was more viscous, approximately nineteen milliliters (19 mL) of bone defect filler was packed into a fifty-milliliter (50 mL) polypropylene graduated cylinder with a thermocouple mounted on the container surface at the five-milliliter (5 mL) level for measuring the exothermic temperature. For Exemplary Embodiments 5-7, which were also more viscous, approximately twenty-six milliliters (26 mL) of bone defect filler was packed into a fifty-milliliter (50 mL) polypropylene graduated cylinder with a thermocouple mounted on the container surface at the ten-milliliter (10 mL) level for measuring the exothermic temperature.

The peak exothermic temperatures of Exemplary Embodiments 1-7, without water contamination, were all lower than the peak exothermic temperature of the control. Additionally, as the concentration of particulate polymer 16 was increased, i.e. from Exemplary Embodiments 1-4 to Exemplary Embodiments 5-7, the peak exothermic temperature was further reduced. This reduction in peak exothermic temperature is beneficial because the exothermic heat from the bone defect filler 10 will cause less cell damage to the patient than conventional polyurethane bone defect fillers, which may result in faster biological recovery.

Figure 15:
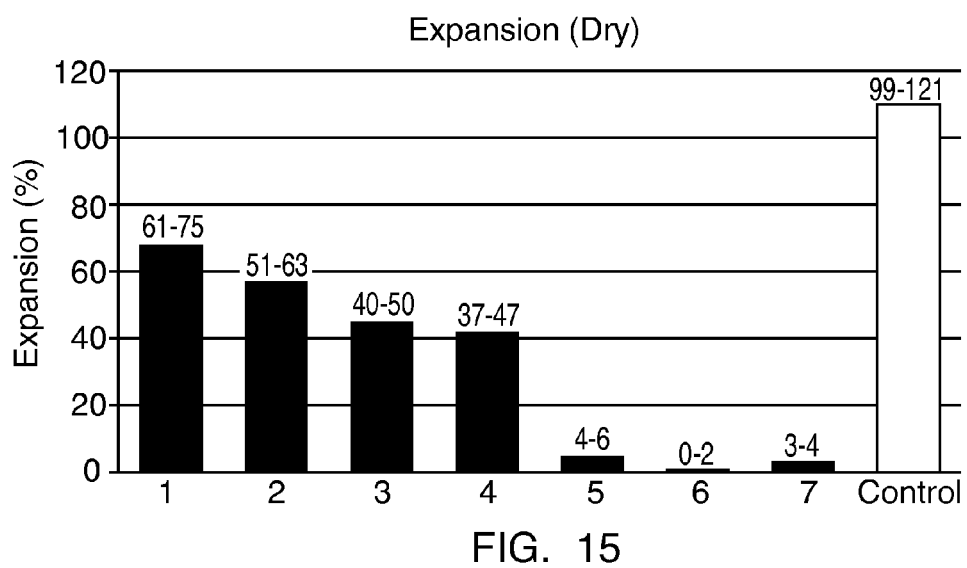
FIG. 15 is a bar graph of expansion of the Exemplary Embodiments of FIG. 11 during polymerization.

Referring to FIG. 15, the expansion of Exemplary Embodiments 1-7 and the control were measured concurrently with the test for the peak exothermic temperature. Exemplary Embodiments 1-7 and the control were polymerized in fifty-milliliter (50 mL) graduated cylinders, as discussed above, for a period of twenty-four (24) hours. After the twenty-four (24) hour period, the final volume of each sample was measured and total expansion of the bone defect filler as a percentage of initial volume was calculated using the equation:

$$\text{Expansion} = \frac{V_F - V_I}{V_I};$$

where:
 $V_F$ is the final volume of the sample; and
 $V_I$ is the initial volume of the sample.

Exemplary Embodiments 1-7 all expanded to a lesser degree than the control during formation without water contamination. Additionally, as the concentration of particulate polymer 16 increased, i.e. from Exemplary Embodiments 1-4 to Exemplary Embodiments 5-7, the expansion of the bone defect filler 10 further reduced when compared to the control. This reduction in expansion is due, at least in part, to the reduction in biocompatible polymeric material that is polymerizing, i.e. the particulate polymer 16 is already fully cured so only the polymeric binder 18 is polymerizing. Thus, as the concentration of the particulate polymer 16 is increased and, conversely, as the concentration of the polymeric binder 18 is decreased, the bone defect filler 10 expands to a lesser degree. Additionally, expansion of the bone defect filler 10 is also affected by the size of the particles 24 of the particulate polymer 16. For instance, as particle size increases at lower concentrations, i.e. from Exemplary Embodiment 1 to Exemplary Embodiment 4, expansion of the bone defect filler 10 decreases. Thus, in some embodiments of the present invention, particularly those with larger particles 24, the polymeric binder 18 may expand within the voids 20 formed between the particles 24 of the particulate polymer 16, thereby further reducing expansion. This reduction in expansion over conventional polyurethane bone defect fillers allows the doctor to more readily control placement of the bone defect filler 10 during implantation.

Figure 16:
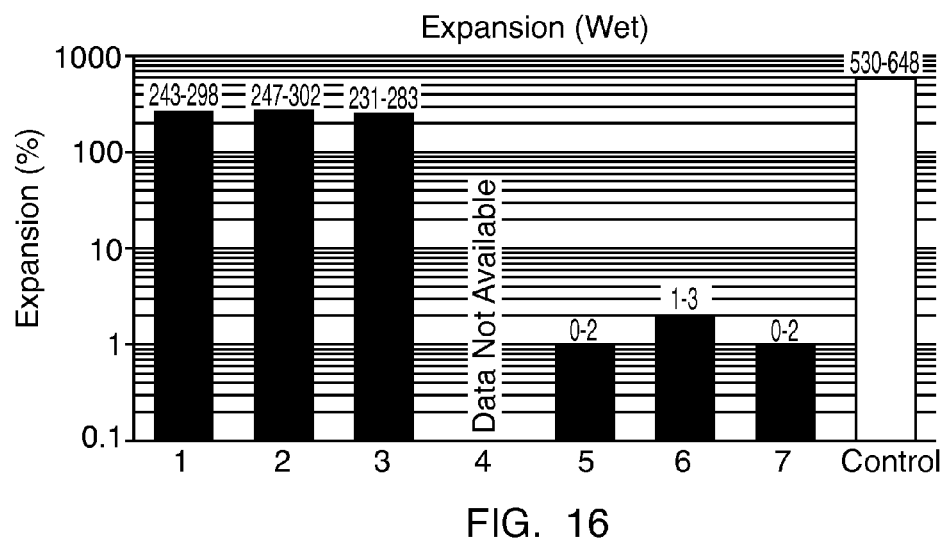
FIG. 16 is a bar graph of the effect on the expansion of the Exemplary Embodiments of FIG. 15 due to water contamination.

Additionally, referring to FIG. 16, the Expansion of Exemplary Embodiments 1-7 and the control was measured for specimens contaminated with water according to the same procedure used for the tests without contamination. For Exemplary Embodiments 1-4, a lower material starting volume was required to accommodate the expansion within graduated cylinders selected for use. For Exemplary Embodiments 1-3 and the control, approximately six milliliters (6 mL) of contaminated bone defect filler was poured into a fifty-milliliter (50 mL) polypropylene graduated cylinder. For Exemplary Embodiment 4, which was more viscous, approximately eight milliliters (8 mL) of contaminated bone defect filler and water was packed into a fifty-milliliter (50 mL) polypropylene graduated cylinder. For Exemplary Embodiments 5-7, volumes were consistent with those described for the case without water contamination. It can be seen that the bone defect filler 10 of Exemplary Embodiments 1-7 is less susceptible to unwanted expansion caused by water contamination than conventional polyurethane bone defect fillers. Furthermore, as the concentration of the particulate polymer 16 in the bone defect filler 10 is increased, i.e. from Exemplary Embodiments 1-3 to Exemplary Embodiments 5-7, the susceptibility of the bone defect filler 10 to water contamination is further reduced.

Figure 17:
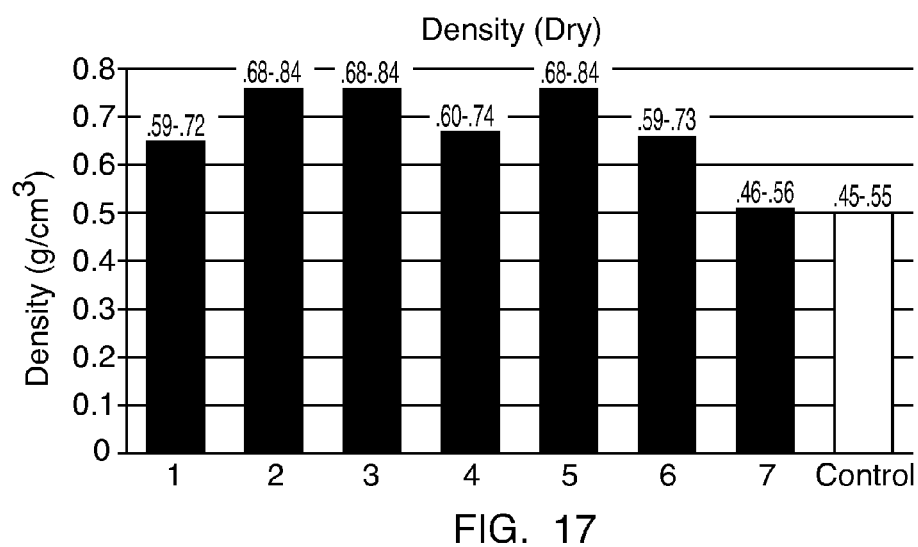
FIG. 17 is a bar graph of density of the Exemplary Embodiments of FIG. 14 after polymerization.
Figure 18:
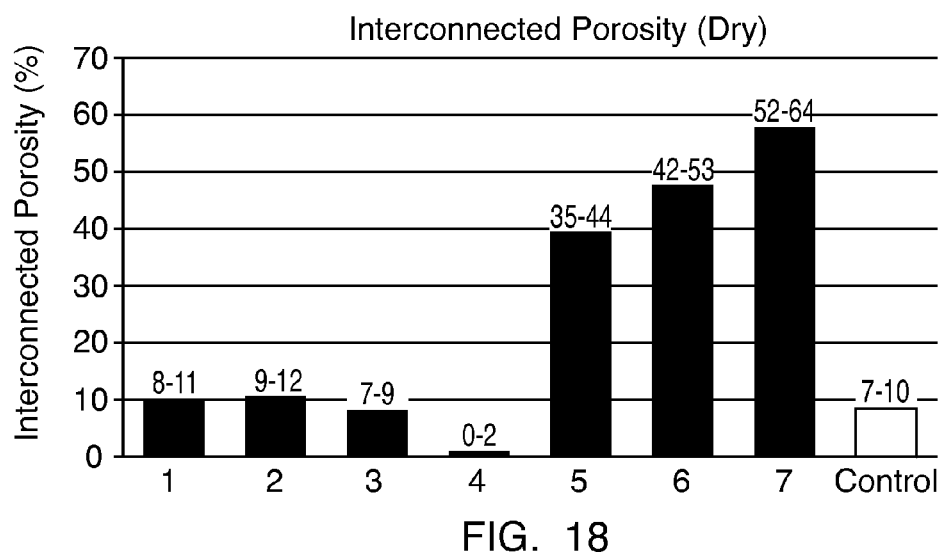
FIG. 18 is a bar graph of pore interconnectivity of the Exemplary Embodiments of FIG. 17.

Referring to FIG. 17, the densities for Exemplary Embodiments 1-7 and for the control were calculated using the final volume of each sample measured in the expansion test, without contamination. After each sample had cured, the samples were removed from the polypropylene graduated cylinders and the mass of each sample was measured. The densities for Exemplary Embodiments 1-7 and the control were then calculated by dividing the mass by the final volume. As seen, the densities of Exemplary Embodiments 1-7 appear to be greater than that of the control. This increase in density relative to the control is, at least in part, due to the reduced expansion of the bone defect filler 10 discussed above in connection with FIG. 15. The density increase of Exemplary Embodiments 1-7 also corresponds to a proportionate loss in total porosity when compared to the control. This loss in total porosity would lead one skilled in the art to believe that the bone defect filler 10 would not promote bone ingrowth and osteoconduction as well as the control. However, Referring to FIG. 18, it can be seen that the bone defect filler 10 has superior porous interconnectivity than the control, particularly at higher concentration, i.e. in Exemplary Embodiments 5-7 where the percent of interconnected porosity exceeds the preferred 30% minimum value, but also at lower concentrations. Since an open pore structure promotes better bone ingrowth than a closed pore structure, the higher degree of pore interconnectivity in the bone defect filler 10 may promote bone ingrowth, at least as well, if not better than the substantially closed pore structure of conventional polyurethane bone defect fillers, even in light of the reduction in total porosity. To calculate the interconnected porosity of the Exemplary Embodiments 1-7 and the control, mineral spirits were added to fifty-milliliter (50 mL) graduated cylinders and the initial volume of the mineral spirits was recorded for each graduated cylinder. Plugs of known volume of the Exemplary Embodiments 1-7 and the control were then placed in the graduated cylinders and the graduated cylinders were agitated in a sonicator for approximately thirty (30) minutes to allow fluid infiltration into the open pores and/or voids of the porous structure. The final volume of the fluid in each graduated cylinder, with the submerged bone defect filler plug, was then measured and recorded. The percentage of interconnected porosity was then calculated using the equation:

$$\text{Interconnected\_Porosity} = \left(1 - \frac{V_F - V_I}{V_P}\right) \times 100;$$

where:

$V_F$ is the final liquid volume measured in the graduated cylinder;

$V_I$ is the initial liquid volume measured in the graduated cylinder; and $V_P$ is the bulk volume of the plug for the appropriate sample.

Figure 19:
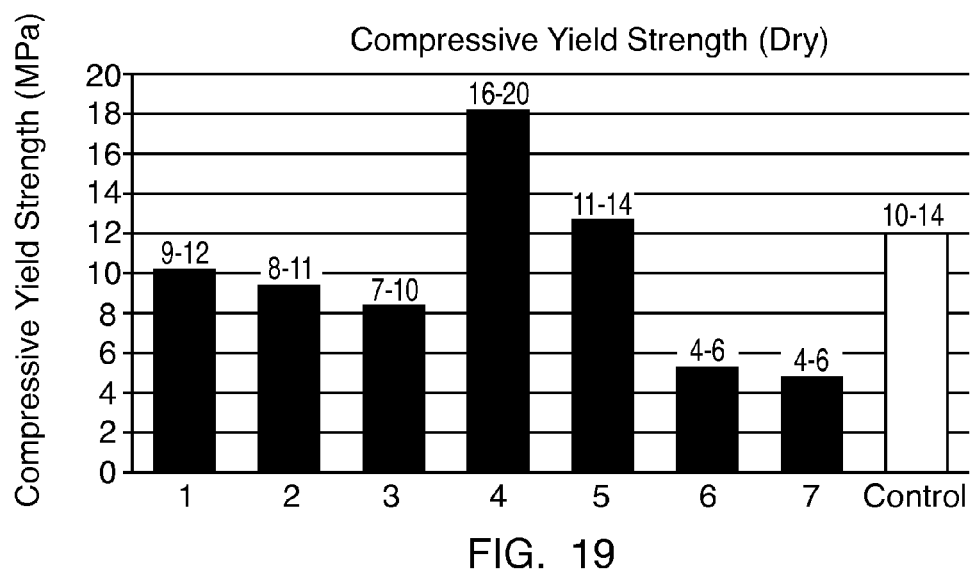
FIG. 19 is a bar graph of the compressive yield strength of the Exemplary Embodiments of FIG. 17.
Figure 20:
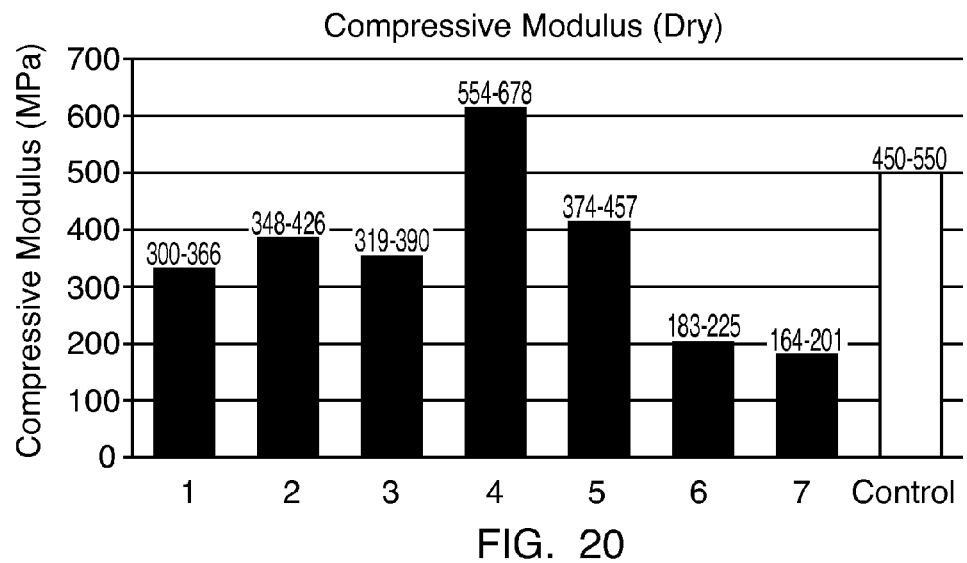
FIG. 20 is a bar graph of the compressive modulus of the Exemplary Embodiments of FIG. 17.

FIGS. 19 and 20 show the compressive yield strength and compressive modulus of the Exemplary Embodiments according to the ASTM D695 standard test method for compressive properties of rigid plastics, calculated using a 0.2% offset method. It can be seen that the compressive yield strength and compressive modulus of some of the fully cured Exemplary Embodiments are greater than the control and those of other fully cured Exemplary Embodiments are lower than the control.

The ultimate tensile stress of Exemplary Embodiments 1-7 was also tested using dumbbell shaped specimens of each Exemplary Embodiment. Each specimen had a thickness of approximately five millimeters (5 mm) and a width of approximately thirteen millimeters (13 mm) in the gauge region of the dumbbell shaped specimen. The tensile stress of each specimen was measured while the specimen was pulled in tension at twelve and seven tenths of a millimeter per minute (12.7 mm/min) until failure of the specimen in the gauge region. The ultimate tensile stress measured for Exemplary Embodiments 1-6 was greater than two megapascals (2 MPa). The ultimate tensile stress measured for Exemplary Embodiment 7 was greater than one and five tenths megapascals (1.5 MPa).

Thus, one skilled in the art will be able to select an appropriate size, shape and concentration of particulate polymer 16 for the bone defect filler 10 depending upon the mechanical properties, balanced with the desired pore interconnectivity, required for a particular application of the bone defect filler 10.

Figure 21:
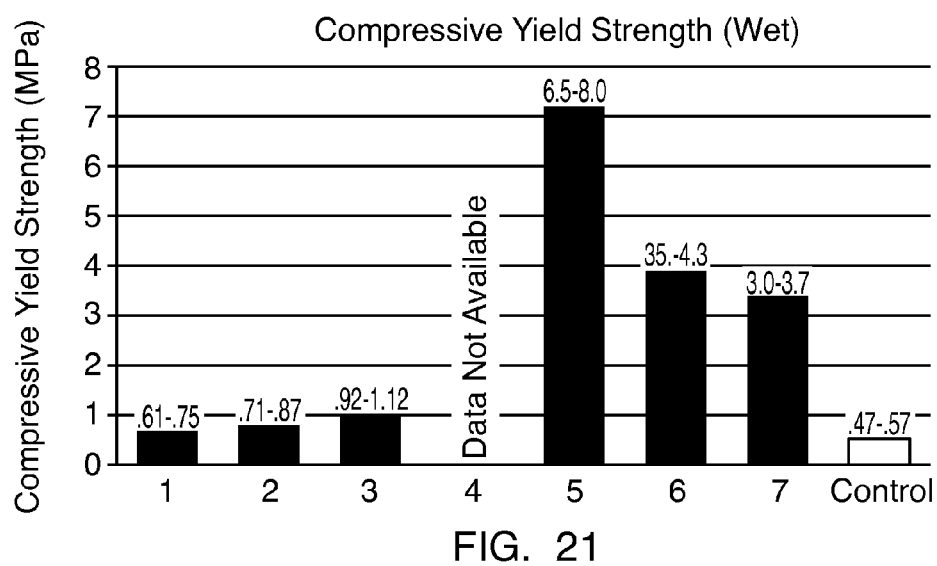
FIG. 21 is a bar graph of the effect on the compressive yield strength of FIG. 19 due to water contamination during polymerization.
Figure 22:
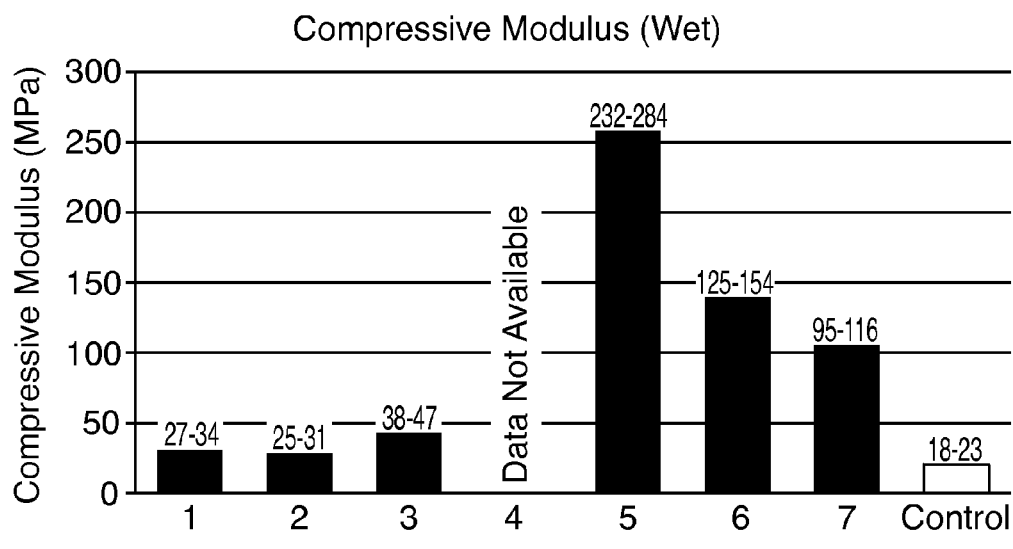
FIG. 22 is a bar graph of the effect on the compressive modulus of FIG. 20 due to water contamination during polymerization.

Additionally, referring to FIGS. 21 and 22, the Exemplary Embodiments are less susceptible to a reduction in compressive yield strength and compressive modulus due to contamination by water during polymerization than the control. Thus, depending upon the intended application for the bone defect filler 10, one skilled in the art may also consider the likelihood of contamination and the susceptibility to contamination of the bone defect filler 10.

Figure 23:
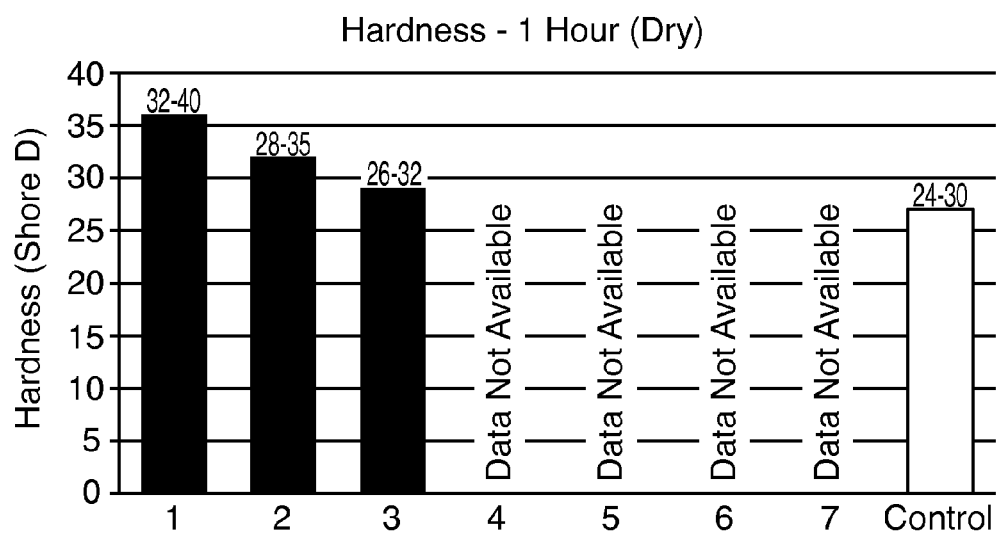
FIG. 23 is a bar graph of hardness of the Exemplary Embodiments of FIG. 14 after one hour of polymerization.
Figure 24:
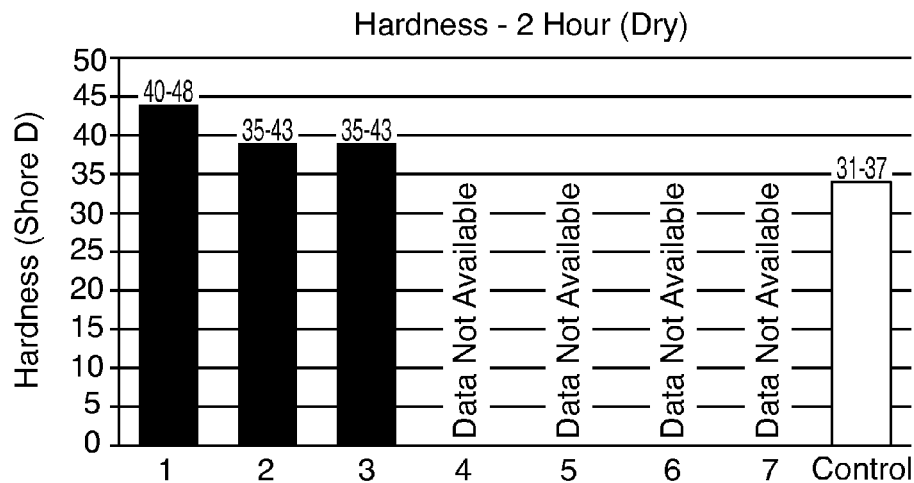
FIG. 24 is a bar graph of the hardness of the Exemplary Embodiments of FIG. 14 after two hours of polymerization.
Figure 25:
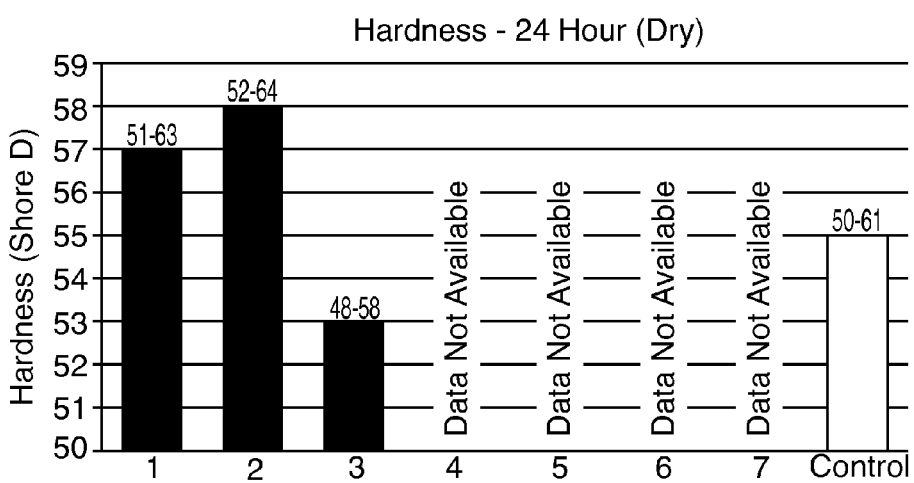
FIG. 25 is a bar graph of the hardness of the Exemplary Embodiments of FIG. 14 after twenty-four hours of polymerization.

Referring to FIGS. 23-25, the Exemplary Embodiments of bone defect filler 10 attain greater hardness than that of the control within the first hour of polymerization, when measured using a Shore D durometer, and maintain comparable hardness until fully cured. Thus, the procedure for implanting bone defect filler 10 may remain substantially the same as the procedure currently being employed to implant convention polyurethane bone defect fillers. As seen in FIGS. 23-25, the hardness for Exemplary Embodiments 4-7 could not be measured due to the porous structure of each embodiment.

Accordingly, the bone defect filler 10, 110, 210, 310, 410, 510 provides an improved bone defect filler having an open cell porous structure 22, 122, 222, 322, 422, 522 that promotes bone ingrowth and osteoconduction after implantation more readily than conventional bone defect fillers. Additionally, the bone defect filler 10, 110, 210, 310, 410, 510 further improves healing by reducing exothermic temperatures when compared to conventional polyurethane bone defect fillers, thereby causing less cellular damage to the patient.

The bone defect filler 10, 110, 210, 310, 410, 510 is also advantageous because it may be provided to a doctor in an easy to use kit 40 with pre-measured components. Furthermore, the bone defect filler 10, 110, 210, 310, 410, 510 provides for easier handling and more precise implantation over conventional polyurethane bone defect fillers by reducing expansion.

The bone defect filler 10, 110, 210, 310, 410, 510 is also advantageous over conventional polyurethane bone void fillers because the bone defect filler 10, 110, 210, 310, 410, 510 may be formed to have similar mechanical properties to conventional polyurethane bone void fillers while being far less susceptible to contamination during formation, which may severely compromise the mechanical integrity of the bone void filler.

Although this invention has been shown and described with respect to the detailed embodiments thereof, it will be understood by those skilled in the art that various changes in form and detail thereof may be made without departing from the spirit and the scope of the invention.

What is claimed is:

1. A bone defect filler comprising:
   a particulated polyurethane having granular particles with diameters between 0.8 millimeters and 1.6 millimeters at a concentration between 50% and 70% of the mass of the bone defect filler or 65% and 90% of the volume of the bone defect filler; and
   a polyurethane binder of substantially the same material composition as the particulated polyurethane binding the particulated polyurethane to form a porous structure of polyurethane material composition having an interconnected porosity greater than 30% of total volume of the bone defect filler.

2. A bone defect filler comprising:
a particulated polyurethane having granular particles with diameters between 1.6 millimeters and 3.2 millimeters at a concentration between 50% and 70% of the mass of the bone defect filler or 65% and 90% of the volume of the bone defect filler; and
a polyurethane binder of substantially the same material composition as the particulated polyurethane binding the particulated polyurethane to form a porous structure of polyurethane material composition having an interconnected porosity greater than 30% of total volume of the bone defect filler.

3. The bone defect filler according to claim 1, wherein the particulated polyurethane and the polyurethane binder are biocompatible polyurethane materials.

4. The bone defect filler according to claim 1, wherein the polyurethane binder is substantially liquid.

5. The bone defect filler according to claim 1, wherein the interconnected porosity is generally suitable for promoting bone growth therein.

6. The bone defect filler according to claim 1, wherein the particulated polyurethane is porous.

7. The bone defect filler according to claim 1, wherein the bone defect filler is adhesive.

8. The bone defect filler according to claim 1, wherein ultimate tensile stress of the bone defect filler is greater than 1.5 megapascals when the bone defect filler is cured.

9. The bone defect filler according to claim 1, wherein compressive yield strength of the bone defect filler is greater than 3 megapascals when the bone defect filler is cured.

10. The bone defect filler according to claim 2, wherein the particulated polyurethane and the polyurethane binder are biocompatible polyurethane materials.

11. The bone defect filler according to claim 2, wherein the polyurethane binder is substantially liquid.

12. The bone defect filler according to claim 2, wherein the interconnected porosity is generally suitable for promoting bone growth therein.

13. The bone defect filler according to claim 2, wherein the particulated polyurethane is porous.

14. The bone defect filler according to claim 2, wherein the bone defect filler is adhesive.

15. The bone defect filler according to claim 2, wherein ultimate tensile stress of the bone defect filler is greater than 1.5 megapascals when the bone defect filler is cured.

16. The bone defect filler according to claim 2, wherein compressive yield strength of the bone defect filler is greater than 3 megapascals when the bone defect filler is cured.

* * * * *